United States Patent [19]

Iverson

[11] Patent Number: 5,961,909
[45] Date of Patent: Oct. 5, 1999

[54] METHOD OF MANUFACTURE OF TISSUE-CONFORMABLE ELECTRODES

[75] Inventor: Alfred A. Iverson, Wayzata, Minn.

[73] Assignee: PMT Corporation, Chanhassen, Minn.

[21] Appl. No.: 08/922,941

[22] Filed: Sep. 3, 1997

[51] Int. Cl.[6] .............................. B29C 41/22; B29C 70/88
[52] U.S. Cl. ........................ 264/219; 264/255; 264/277; 264/272.14; 264/272.15; 425/123
[58] Field of Search .................................. 264/219, 255, 264/272.14, 272.15, 275, 277, 279, 301, 272.11, 272.17; 425/275; 156/242, 245

[56] References Cited

U.S. PATENT DOCUMENTS

| | | | |
|---|---|---|---|
| 3,866,660 | 2/1975 | Gill | 164/108 |
| 4,735,208 | 4/1988 | Wyler et al. | |
| 4,869,255 | 9/1989 | Putz | |
| 5,037,497 | 8/1991 | Stypulkowski | 156/245 |
| 5,498,388 | 3/1996 | Kodai et al. | 264/263 |

*Primary Examiner*—Jan H. Silbaugh
*Assistant Examiner*—Suzanne E. Mason
*Attorney, Agent, or Firm*—Anthony G. Eggink

[57] ABSTRACT

A tissue-conformable electrode for monitoring tissue electrical activity of the type having a plurality of contacts embedded in a flexible matrix material and custom built to conform to the contours of a portion of the tissue to be monitored consists of a flexible matrix pre-shaped to conform to the contour of a portion of the tissue to be monitored; a plurality of contacts embedded in the matrix and protruding through the matrix to contact the tissue; and lead wires engaging the electrical contacts and exiting the electrode for making electrical connection with monitoring equipment. A method of manufacture of a tissue-conformable electrode comprises the steps of constructing a mold with a plurality of contact locations, the surface of the mold having the contour of a portion of the tissue to be monitored; placing a first layer of tacky matrix material on the mold; placing a plurality of contacts on the first layer of tacky matrix material at the contact locations, the contacts protruding through the first layer to contact the mold, the first layer holding the contacts in engagement with the mold, the contacts having a plurality of lead wires associated therewith; placing a second layer of matrix material on the mold over the contacts, thereby embedding the contacts within the second layer; hardening the matrix material to form an electrode with embedded contacts; and removing the electrode from the mold.

27 Claims, 4 Drawing Sheets

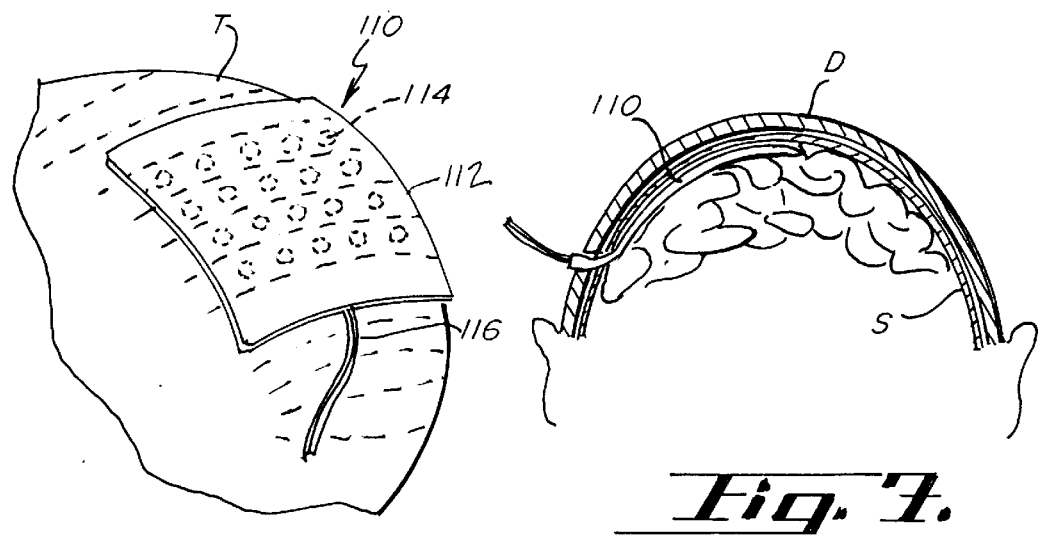
Fig. 6.
Fig. 7.
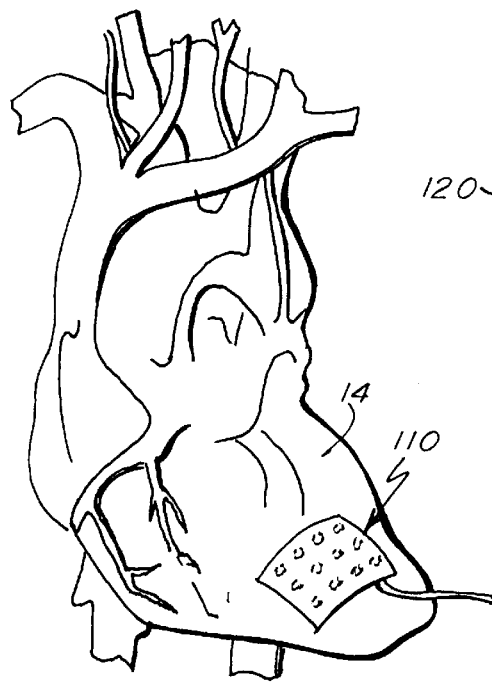
Fig. 8.
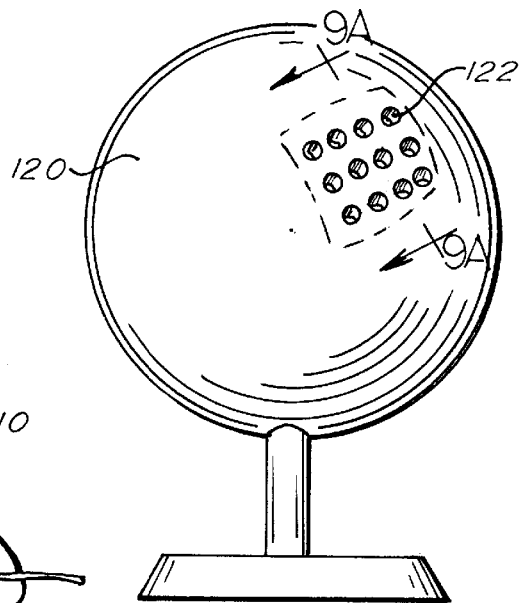
Fig. 9.
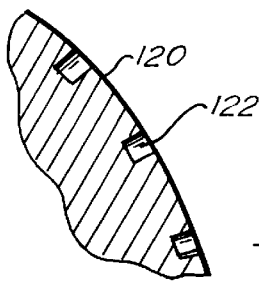
Fig. 9A.

METHOD OF MANUFACTURE OF TISSUE-CONFORMABLE ELECTRODES

BACKGROUND OF THE INVENTION

This invention is related generally to electrodes for monitoring tissue electrical activity.

Surgical removal of epileptogenic brain is indicated for treatment of many medically refractory focal seizure disorders. One of the important factors in providing good results from such surgery is the degree of accuracy in identifying epileptogenic foci. Various methods have been used in attempting to determine epileptogenic foci, and all, of course, involve sensing of cortical electrical activity using electrical contacts applied in various ways.

Standard scalp contacts have been used for many years, but accurate localization is usually very difficult with recordings obtained from such contacts. Therefore, many epilepsy centers in recent years have used intracranial recording techniques to better define regions of cortical epileptogenicity.

Intracranial recording techniques have used either of two different types of electrodes—intracortical depth electrodes or subdural strip electrodes. The far more commonly used technique of intracranial recording uses intracortical depth electrodes, but other techniques using subdural strip electrodes, first utilized many years ago, have been shown to be relatively safe and valuable alternatives.

The relative safety of subdural strip electrodes lies in the fact that, unlike depth electrodes, they are not invasive of brain tissue. Depth electrodes are narrow, typically cylindrical dielectric structures with contact bands spaced along their lengths. Such electrodes are inserted into the brain in order to establish good electrical contact with different portions of the brain. Subdural strip electrodes, on the other hand, are generally flat strips supporting contacts spaced along their lengths. Such strip electrodes are inserted between the dura and the brain, along the surface of and in contact with the brain, but not within the brain.

A typical subdural strip electrode of the prior art is shown in FIGS. 1–3 and is disclosed in U.S. Pat. No. 4,735,208. The '208 patent discloses a subdural strip electrode 10 having an elongated flexible silicone dielectric strip 14, a plurality of spaced aligned flat electrical stainless steel contact disks 16 held within dielectric strip 14, and lead wires 18 exiting strip 14 from a proximal end 20 thereof.

Dielectric strip 14 of strip electrode 10 has front and back dielectric layers 22 and 24, respectively. Each front layer 22 has a front layer opening 26 for each contact disk 16. Openings 26 are circular and somewhat smaller in diameter than contact disks 16. Front and back layers 22 and 24 are sealed together by adhesive and/or heat such that they form, in essence, an integral dielectric strip.

As can be seen in FIGS. 2 and 3, the subdural strip electrodes of the prior art are predominately rectangular in cross-section. Other subdural strip electrodes of the prior art have a circular or round cross section.

As can be seen in FIGS. 4 and 5, prior art subdural strip electrodes that have a rectangular (FIG. 4) or round (FIG. 5) cross-section do not optimize the amount of surface area of the electrode E in contact with the cortical surface S. As the electrode E is inserted between the dura D and the cortical surface S, downward pressure is exerted by the dura on the electrode, which in turn exerts pressure on the cortical surface. Such pressure causes the cortical surface S to slightly deflect downward, as shown in the Figures. Prior art rectangular or round electrodes cannot follow this deflection, resulting, in the case of a rectangular electrode (FIG. 4), in the electrode contacting the surface S primarily at the edges; and in the case of the round electrode (FIG. 5), in the electrode contacting the surface S along an arc.

A variety of other electrodes have been used for insertion into other tissue, such as the spinal cord, musculature, and heart. However, none of these electrodes have been custom-built to conform to the shape of a portion of the tissue in which they are being inserted, and thus electrical contact between the tissue and the electrode has not been optimized, because of the same type of problem as noted above with reference to subdural strip electrodes.

There is a need for a tissue-conformable electrode which can be custom-built to conform to the contours of a portion of the tissue in which or on which the electrode is being placed.

SUMMARY OF THE INVENTION

A tissue-conformable electrode for monitoring tissue electrical activity of the type having a plurality of contacts embedded in a flexible matrix material and custom built to conform to the contours of a portion of the tissue to be monitored consists of a flexible matrix pre-shaped to conform to the contour of a portion of the tissue to be monitored; a plurality of contacts embedded in the matrix and protruding through the matrix to contact the tissue; and lead wires engaging the electrical contacts and exiting the electrode for making electrical connection with monitoring equipment. A method of manufacture of a tissue-conformable electrode comprises the steps of constructing a mold with a plurality of contact locations, the surface of the mold having the contour of a portion of the tissue to be monitored; placing a first layer of tacky matrix material on the mold; placing a plurality of contacts on the first layer of tacky matrix material at the contact locations, the contacts protruding through the first layer to contact the mold, the first layer holding the contacts in engagement with the mold, the contacts having a plurality of lead wires associated therewith; placing a second layer of matrix material on the mold over the contacts, thereby embedding the contacts within the second layer; hardening the matrix material to form an electrode with embedded contacts; and removing the electrode from the mold.

A principal object and advantage of the present invention is that the tissue-conformable electrode can be custom-built to conform to the contours of the tissue to be monitored, thus optimizing electrical contact between the tissue and the electrode.

Another object and advantage of the present invention is that the tissue-conformable electrode has greater versatility in its electrode layout than earlier electrodes.

Another object and advantage of the present invention is that the tissue-conformable electrode may be thinner and more supple than earlier electrodes.

Another object and advantage of the present invention is that the method of manufacture allows precise control over placement of the electrode contacts on the electrode.

Another object and advantage of the present invention is that the ease of manufacture is greater and the cost of manufacture is less than previous electrodes.

Another object and advantage of the present invention is that it allows for varying the amount by which the electrode contacts protrude from the electrode.

Another object and advantage of the present invention is that it allows for random or irregular electrode shapes without the need for expensive multiple-piece molds.

BRIEF DESCRIPTION OF THE DRAWINGS

FIG. 6 is a schematic of a tissue-conformable electrode of the present invention contacting a tissue.

FIG. 7 is a schematic of a tissue-conformable electrode of the present invention pre-shaped to the contour of the brain surface and inserted between the dura and the brain surface.

FIG. 8 is a schematic of a tissue-conformable electrode of the present invention pre-shaped to the surface of the heart and placed on the surface of the heart.

FIG. 9 is a schematic of a mold for manufacturing the tissue-conformable electrode of the present invention.

FIG. 9A is a cross-section along the lines 9A of FIG. 9.

DETAILED DESCRIPTION OF THE PREFERRED EMBODIMENTS

Figure 1:
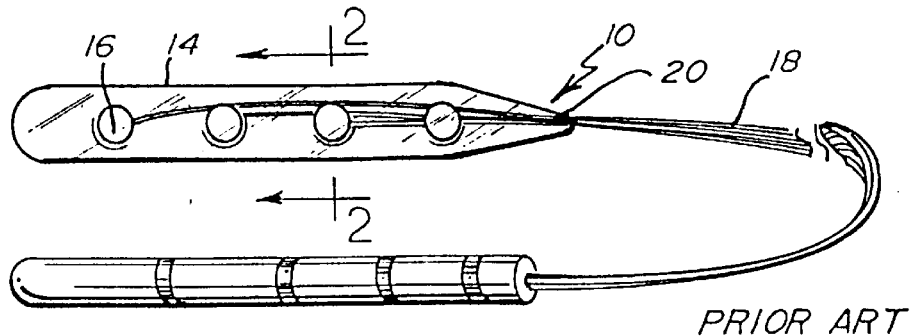
FIG. 1 is an top view of a prior art subdural strip electrode.
Figure 2:
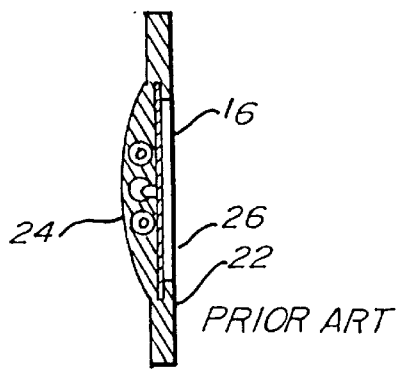
FIG. 2 is a cross-section along the lines 2 of FIG. 1.
Figure 3:
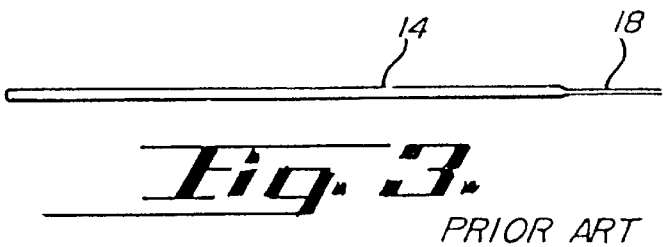
FIG. 3 is a side elevational view of the prior art electrode of FIG. 1.
Figure 4:
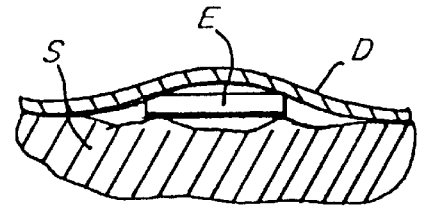
FIG. 4 is a sectional view of a rectangular prior art electrode inserted between the dura and the brain surface.
Figure 5:
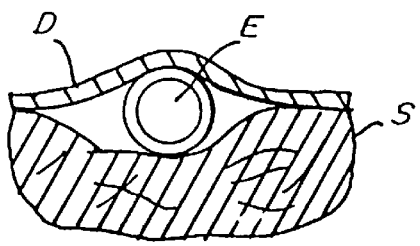
FIG. 5 is a sectional view of a round prior art electrode inserted between the dura and the brain surface.

The tissue-conformable electrode of the present invention is shown in the Figures as reference numeral 110.

FIG. 6 shows schematically a tissue-conformable electrode 110 pre-shaped to conform to a tissue T. The tissue T may be any body tissue such as, without limitation, the brain, spinal cord, musculature, heart, or other internal organs.

The tissue-conformable electrode 110 consists of a flexible matrix 112 adapted to be molded outside the body to conform to the contour of a portion of the tissue T to be monitored, a plurality of electrical contacts 114 embedded in the flexible matrix 112 and protruding through the matrix to contact the tissue T, and lead wires 116 engaging the electrical contacts 114 and exiting the electrode 110 for making electrical connection with monitoring equipment (not shown). As shown in the drawings, the tissue-conformable electrode 110 is a generally thin flexible structure.

The tissue-conformable electrode may be molded outside the body to conform to the contour of a portion of any tissue. All that is required is a mold having the contour of the portion of tissue to be monitored. The mold shape may be determined by any of a variety of measurement techniques, such as X-ray imaging, MRI, CAT-scans, measurement of organs of cadavers, or other measurement techniques.

FIG. 7 shows the tissue-conformable electrode 110 pre-shaped to conform to the contour of a portion of the brain surface S and inserted between the dura D and brain surface S.

FIG. 8 shows the tissue-conformable electrode 110 pre-shaped to conform to the a portion of the surface of the heart H and placed on the surface of the heart H for monitoring the electrical activity of the heart.

A method of manufacture of the tissue-conformable electrode consists of the following steps.

First, a mold 120 is constructed outside the body having the contour of the portion of tissue to be monitored. The locations 122 where the electrical contacts are to be placed are either marked on the surface of the mold or the locations 122 are indented in the surface of the mold (FIGS. 9 and 9A).

Figure 10:
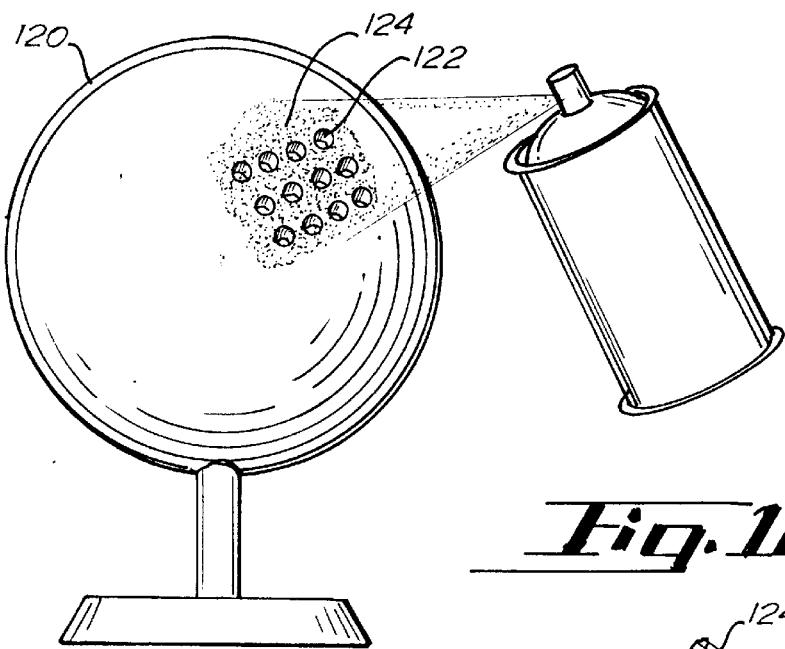
FIG. 10 shows a thin layer of matrix material being sprayed onto the mold.

Next, a first layer of tacky matrix material 124 is placed on the mold 120 (FIG. 10). The purpose of this first layer is to hold the contacts in engagement with the mold. Accordingly, the first layer 124 need not be very thick. The first layer 124 may be applied by any of a variety of techniques. For example, the mold may be dipped in the matrix material, the matrix material may be sprayed onto the mold, the matrix material may be painted onto the mold, and the matrix material may be poured onto the mold.

Figure 11:
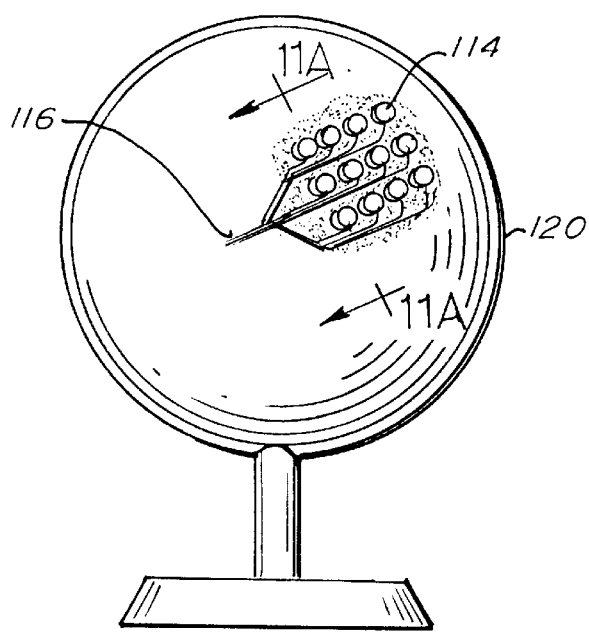
FIG. 11 shows electrode contacts and lead wires being inserted in the mold on the layer of matrix material.
Figure 11A:
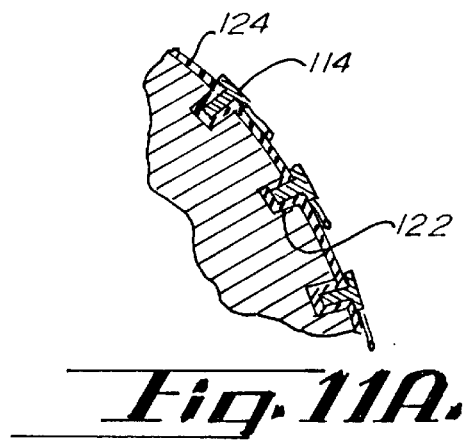
FIG. 11A is a cross section along the lines 11A of FIG. 11.

Next, the electrical contacts 114 are placed on the first layer of tacky matrix material 124 at the contact locations 122 so that the contacts 114 protrude through the first layer 124 to contact the mold 120 (FIGS. 11 and 11A). The amount of protrusion may be varied by varying the depth of the indentations in the surface of the mold. If the contacts are to be flush with the surface of the electrode, then very little or no indentation would be used. If the contacts are to protrude substantially above the surface of the electrode, then substantial indentation would be used.

The first layer of tacky matrix material will preferably hold the contacts in engagement with the mold.

The contacts 114 may have a plurality of lead wires 116 associated with them. The lead wires 116 may also be held in engagement with the mold by the first layer of tacky material 124.

Figure 12:
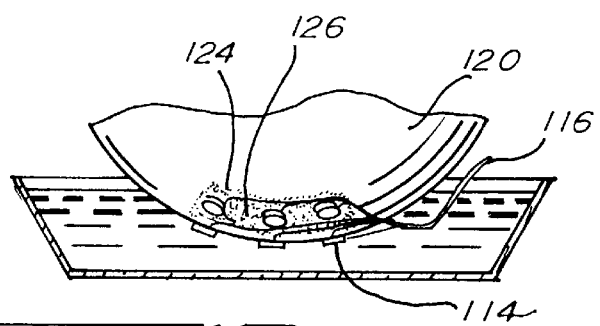
FIG. 12 shows a mold being dipped into a dispersion of matrix material to form a second layer of matrix material over the electrode contacts.

Next, a second layer of matrix material 126 is placed on the mold over the contacts 114, thereby embedding the contacts 114 within the second layer 126. The second layer 126 may be applied by any of a variety of techniques. For example, the mold may be dipped in the matrix material (FIG. 12), the matrix material may be sprayed onto the mold, the matrix material may be painted onto the mold, and the matrix material may be poured onto the mold. The matrix material for the second layer may be different from the matrix material used for the first layer, or it may be the same.

Optionally, additional layers of matrix material are placed on the mold over the contacts, thereby increasing the thickness of the matrix material as desired.

Figure 13:
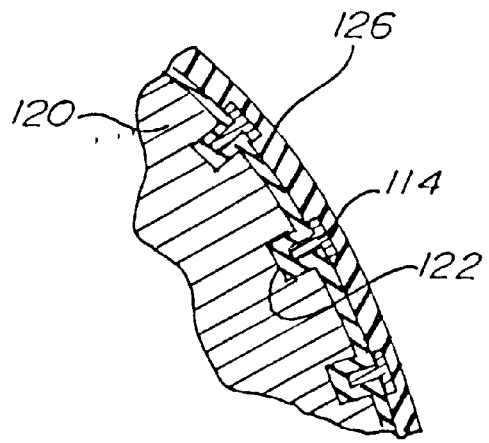
FIG. 13 is a cross-section of the mold after the additional layer of matrix material has been hardened.

Next, the matrix material is hardened to form the electrode with embedded contacts (FIG. 13). The matrix material may be hardened by any of a variety of techniques such as, without limitation, heating, air drying, or vulcanization.

The matrix material may be any substance that can be sprayed, dipped, or poured onto the mold. Examples of matrix materials are a dispersion of silicone rubber or other polymer, latex rubber, varnish, or other air drying compound or vulcanizable compound.

Figure 14:
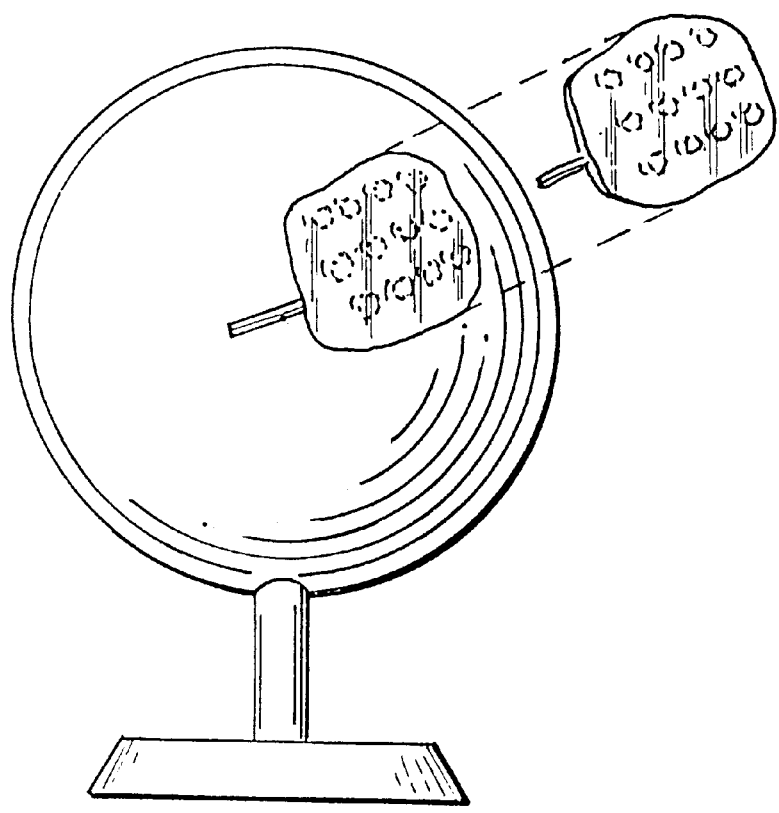
FIG. 14 is a schematic showing the finished electrode being removed from the mold.

Finally, the electrode is removed from the mold (FIG. 14). If necessary, any flashing of matrix material covering the contacts on the side of the mold contacting the tissue is removed. The electrode is trimmed to final shape and size if necessary.

The order of the above steps is not critical for the invention. The contacts may be placed on the mold before, during, or after the first or subsequent layers of matrix material are applied to the mold.

The mold is preferably a mandrel. The mandrel can be made of any material that is formable to the contour of tissue, such as plastic, wood, rubber, or wax. Preferably, the mandrel is made of aluminum or steel.

It will be seen that because of the manufacturing method, the thickness of the electrode can be varied over a wide range. The electrode may be thinner and more supple than earlier electrodes.

The method of manufacture also allows precise control over the placement of the electrical contacts on the electrode.

Because a variety of electrode shapes may be produced, including random or irregular shapes, without the need for expensive multiple-piece molds, the ease of manufacture and cost of manufacture is less than for previous electrodes.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed:

1. A method for manufacturing tissue-conformable electrodes for monitoring tissue electrical activity having a plurality of contacts embedded in a flexible matrix material and custom built to conform to the contours of a portion of tissue to be monitored, comprising the steps of:
   a) constructing a mold having an exterior molding surface with a plurality of contact locations, said molding surface having the contour of the portion of tissue to be monitored;
   b) placing a first layer of tacky matrix material on said molding surface;
   c) placing a plurality of electrical contacts on the first layer of tacky matrix material at said contact locations and pushing said contacts into said first layer, whereby a portion of each said contact protrudes through said first layer to contact said exterior molding surface, the first layer of tacky matrix material adhesively holding the contacts in engagement with the molding surface, the contacts having a plurality of lead wires associated therewith;
   d) placing a second layer of matrix material contiguously over said first layer and said electrical contacts, thereby embedding the contacts within the second layer;
   e) hardening the matrix material to form an electrode with embedded contacts having portions being either flush with or protruding from one side of said electrode for subsequent contact with said tissue; and
   f) removing the electrode from said molding surface.

2. The method of claim 1, wherein the mold is a mandrel.

3. The method of claim 2, wherein the mandrel is made of aluminum or other metal.

4. The method of claim 2, wherein the contact locations are marked on the surface of the mandrel.

5. The method of claim 2, wherein the contact locations are indented in the surface of the mandrel.

6. The method of claim 1, wherein the mold is dipped into the matrix material to form the first layer.

7. The method of claim 1, wherein the first layer of matrix material is sprayed onto the mold.

8. The method of claim 1, wherein the first layer of matrix material is painted onto the mold.

9. The method of claim 1, wherein the first layer of matrix material is poured onto the mold.

10. The method of claim 1, wherein the mold is dipped into the matrix material to form the second layer.

11. The method of claim 1, wherein the second layer of matrix material is sprayed onto the mold.

12. The method of claim 1, wherein the second layer of matrix material is painted onto the mold.

13. The method of claim 1, wherein the second layer of matrix material is poured onto the mold.

14. The method of claim 1, wherein the matrix material is hardened by air drying.

15. The method of claim 1, wherein the matrix material is hardened by vulcanization.

16. The method of claim 1, wherein the matrix material is silicone rubber.

17. The method of claim 1, wherein the matrix material is latex rubber.

18. The method of claim 1, further comprising the steps of placing additional layers of matrix material onto the mold before hardening the matrix material, thereby increasing the thickness of the matrix material.

19. A method for manufacturing tissue-conformable electrodes for monitoring tissue electrical activity having a plurality of contacts embedded in a flexible matrix material having a generally uniform thickness and custom built to conform to the contours of a portion of tissue to be monitored, comprising the steps of:
   a) constructing a mold with an exterior molding surface and with a plurality of predetermined contact locations therein, said exterior surface of the mold having the contour of the portion of tissue to be monitored;
   b) placing a first layer of tacky matrix material on said molding surface;
   c) placing a plurality of contacts on the first layer of tacky matrix material at said contact locations, the contacts protruding through the first layer to contact the contact locations in said molding surface, the first layer holding the contacts in engagement with said molding surface, the contacts having a plurality of lead wires associated therewith;
   d) placing a second layer of matrix material over said first layer and said contacts, thereby embedding the contacts within the second layer;
   e) placing additional layers of matrix material over said first and second layers, and said contacts, thereby increasing the thickness of the matrix material as desired;
   f) hardening the matrix material to form an electrode with embedded contacts having portions protruding from said electrode for subsequent contact with said tissue; and
   g) removing the electrode from said mold surface.

20. A method for manufacturing tissue-conformable electrodes for monitoring tissue electrical activity having a plurality of contacts embedded in a flexible matrix material and custom built to conform to the contours of a portion of tissue to be monitored, comprising the steps of:
   a) constructing a mandrel having an exterior molding surface and having a plurality of predetermined contact locations positioned in said exterior surface of the mandrel, the exterior surface of the mandrel having the contour of the portion of tissue to be monitored;
   b) placing a first layer of tacky material on the mandrel;
   c) placing a plurality of contacts on the first layer of tacky matrix material and pushing said contacts through said first layer, whereby a portion of said contact protrudes through the first layer, the first layer adhesively holding the contacts in engagement with said molding surface, the contacts having a plurality of lead wires associated therewith;

d) placing a second layer of tacky matrix material contiguously over said first layer and said contacts, thereby embedding the contacts within the second layer;

e) placing additional layers of tacky matrix material on the mandrel over the contacts, thereby increasing the thickness of the matrix material as desired;

f) hardening the matrix material to form an electrode with embedded contacts having portions protruding from one side of said electrode for subsequent contact with tissue; and g) removing the electrode from said molding surface.

21. A method for manufacturing tissue-conformable electrodes for monitoring tissue electrical activity having a plurality of contacts embedded in a flexible matrix material and custom built to conform to the contours of a portion of tissue to be monitored, comprising the steps of:

a) constructing a mold having an exterior molding surface having a plurality of contact locations thereon, the surface of said molding surface having the contour of the portion of tissue to be monitored;

b) placing a plurality of contacts on said molding surface at said contact locations, the contacts having a plurality of lead wires associated therewith;

c) placing a first layer of tacky matrix material on said molding surface, the first layer adhesively holding the contacts in engagement with said molding surface;

d) placing a second layer of matrix material on the contiguously over said first layer and said contacts, thereby embedding the contacts within the matrix material;

e) hardening the matrix material to form an electrode with embedded contacts having portions being either flush with or protruding from one side of said electrode for subsequent contact with tissue; and f) removing the electrode from said molding surface.

22. The method of claim 21, further comprising the steps of placing additional layers of matrix material onto the mold, thereby increasing the thickness of the matrix material.

23. The method of claim 1, wherein said contacts provided on the exterior molding surface are indented therein.

24. The method of claim 1, wherein flashing of matrix material is removed from the contacts.

25. The method of claim 19, wherein flashing of matrix material is removed from the contacts.

26. The method of claim 20, wherein flashing of matrix material is removed from the contacts.

27. The method of claim 21, wherein said contacts provided on the exterior molding surface are indented therein and wherein flashing of matrix material is removed from the contacts.

* * * * *